Figure 1:
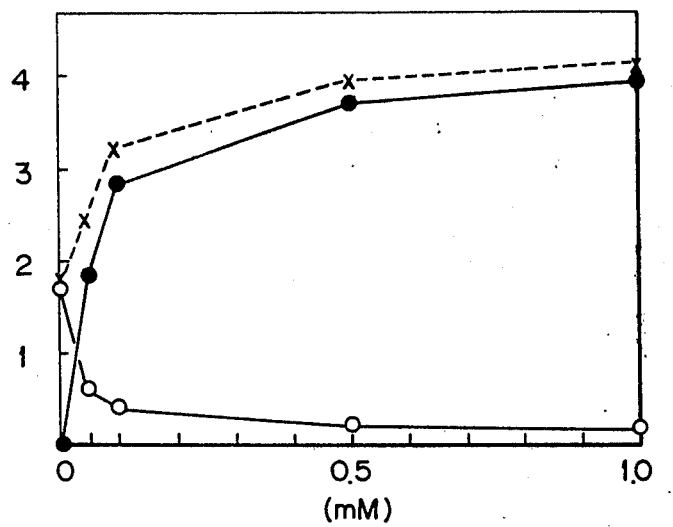

United States Patent [19]

Noyori et al.

[11] 4,446,312

[45] May 1, 1984

[54] C-β-D-XYLOPYRANOSIDE SERIES COMPOUNDS

[75] Inventors: Ryoji Noyori, Aichi; Sakaru Suzuki; Minoru Okayama, both of Nagoya, all of Japan

[73] Assignee: Seikagaku Kogyo Co., Ltd., Tokyo, Japan

[21] Appl. No.: 466,085

[22] Filed: Feb. 14, 1983

Related U.S. Application Data

[63] Continuation-in-part of Ser. No. 319,392, Nov. 9, 1981, abandoned.

[30] Foreign Application Priority Data

Nov. 13, 1980 [JP] Japan .............................. 55-158855

[51] Int. Cl.$^3$ .............................................. C07H 7/02
[52] U.S. Cl. ..................................... 536/1.1; 424/180
[58] Field of Search ......................................... 536/1.1

[56] References Cited

U.S. PATENT DOCUMENTS 3,940,383 2/1976 Fujiwara et al. ..................... 536/4

OTHER PUBLICATIONS

Deleyn et al., "Chem. Abst.", vol. 92, 1980, p. 193427(a).

*Primary Examiner*—Johnnie R. Brown
*Attorney, Agent, or Firm*—Frishauf, Holtz, Goodman & Woodward

[57] ABSTRACT

Disclosed are novel C-β-D-xylopyranoside series compounds which are expected to have an inhibitive effect on cancers, vascular sclerosis, thrombus and the like. The C-β-D-xylopyranoside series compounds are represented by the following general formula:

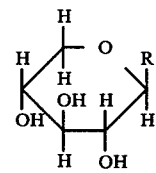

in which R denotes a lower alkyl group having from 1 to 5 carbon atoms.

11 Claims, 3 Drawing Figures

C-β-D-XYLOPYRANOSIDE SERIES COMPOUNDS

This application is a continuation-in-part application of the parent application U.S. Ser. No. 319,392 filed on Nov. 9, 1981, now abandoned.

This invention relates to novel C-β-D-xylopyranoside series compounds, and more particularly to C-β-D-xylopyranoside series compounds which have the properties to change nature and quantity of the glycoconjugate(proteoglycan) existing on the surface of cell membranes and which are thus expected to bring effects to inhibit a transplantable cancer such as Sarcoma-180, vascular sclerosis, thrombus and the like.

It has heretofore been known that O-β-D-xylopyranoside series compounds change quantity of the so-called proteoglycan, which exists at the surface of cell membranes or between cells and which is one of important components constituting organism tissues, and they also greatly alter the properties of the surfaces of a certain type of cell membranes [J. Biochem. 74, 1069–1073 (1973)].

For example, with respect to tumor cells, the O-β-D-xylopyranoside series compounds can change the properties of proteoglycan on the surface of the tumor cells and reduce the quantity thereof so as to strip the tumor cells naked, so to speak. Thus, it is well expected that the O-β-D-xylopyranoside series compounds will enhance the immunity of the living organisms to the tumor cells in order to prevent an attack of tumors and to thereby improve therapeutic effects. However, the O-β-D-xylopyranoside series compounds are liable to be hydrolyzed by enzymes. For example, when such a compound is administered to a human body for the purpose of inhibiting a tumor, the major portion of the administered compound is decomposed to a useless form before showing its effects.

The inventors have found out C-β-D-xylopyranoside series compounds which hardly tend to be hydrolyzed by virtue of enzymes and which can nevertheless maintain the property to alter the nature and the quantity of the proteoglycan existing on the surfaces of cells, and completed the present invention.

An object of the present invention is to provide novel types of C-β-D-xylopyranoside compound.

Namely, the present invention provides C-β-D-xylopyranoside series compounds represented by the following general formula (I):

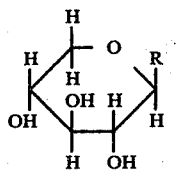

(I)

in which R denotes a lower alkyl group having from 1 to 5 carbon atoms. The compounds represented by the general formula (I) according to the present invention are novel, and R in the general formula (I) may, for example, denote methyl, ethyl, n-propyl, isopropyl, n-butyl, isobutyl, sec-butyl, tert-butyl, n-pentyl, isopentyl or the like.

As examples of the concrete compounds according to the present invention, the following may be mentioned:

1. C-Methyl-β-D-xylopyranoside (C-β-D-xylopyranosylmethane)
2. C-Ethyl-β-D-xylopyranoside (C-β-D-xylopyranosylethane)
3. C-n-Propyl-β-D-xylopyranoside (C-β-D-xylopyranosyl-n-propane)
4. C-Isopropyl-β-D-xylopyranoside (C-β-D-xylopyranosyl-2-propane)
5. C-n-Butyl-β-D-xylopyranoside (C-β-D-xylopyranosyl-n-butane)
6. C-Isobutyl-β-D-xylopyranoside (C-β-D-xylopyranosylisobutane)
7. C-sec-Butyl-β-D-xylopyranoside (C-β-D-xylopyranosyl-sec-butane)
8. C-tert-Butyl-β-D-xylopyranoside (C-β-D-xylopyranosyl-tert-butane)
9. C-n-Pentyl-β-D-xylopyranoside (C-β-D-xylopyranosyl-n-pentane)

The compounds represented by the general formula (I) according to the present invention can be prepared by the following route of reaction:

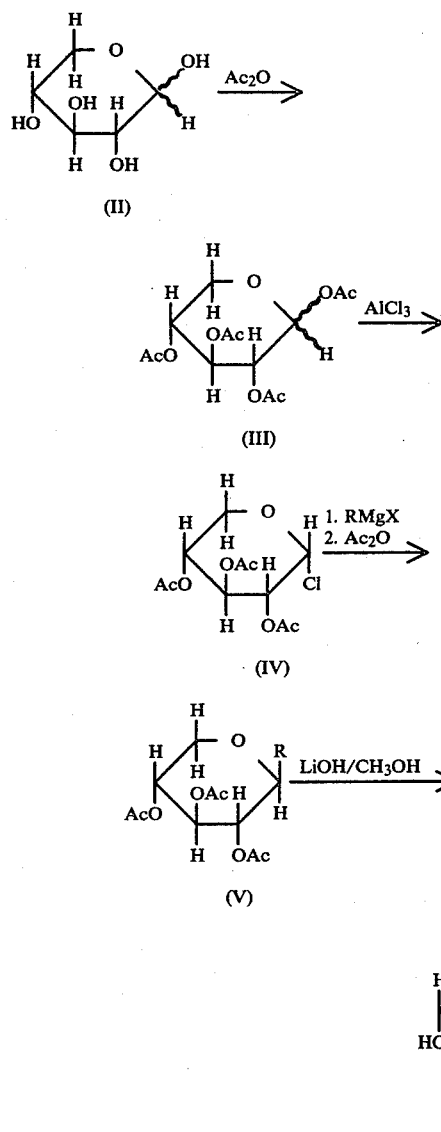

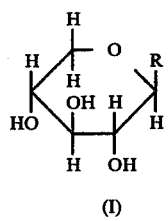

(I)

in which Ac denotes acetyl (CH$_3$CO), X denotes a halogen atom such as a chlorine atom or a bromine atom, and R is as defined above.

That is, D-xylose (II) is acetylated to form a tetraacetate (III) by the method proposed by Hudson et al. [C. S. Hudson, J. M. Johnson, J. Am. Chem. Soc., 37, 2748 (1915)]. The tetraacetate (III) thus obtained is then treated with aluminum chloride to give a compound (IV) by the method proposed by Holland et al. [C. V. Holland, D. Horton, J. S. Jewell, J. Org. Chem., 32, 1818 (1967)]. At this stage, the β-form of compound (IV) is obtained when the tetraacetate (III) is treated with aluminum chloride for a short period of time; the α-form of compound (IV), which is thermodynamically stable, is obtained when the time of the treatment with aluminum chloride is longer. The compound (IV) can be prepared also by treating the D-xylose (II) with acetyl chloride in the presence of zinc chloride [J. Am. Chem. Soc., 37, 2748 (1915) mentioned above].

Thereafter, the obtained compound (IV) is treated with an excess of Grignard reagent, followed by acetylation to give a compound (V). At this stage, both α- and β-forms of the compound (V) are formed. The β-form thereof can be separated from the α-formed by means of chromatography, recrystallization or the like. The thus obtained β-form of the compound (V) is then treated in methyl alcohol with a catalytic amount of a base such as lithium hydroxide or sodium hydroxide to yield the desired compound (I) according to the present invention.

The thus prepared C-β-D-xylopyranoside compounds of the present invention can serve as a satisfactory initiator for the biosynthesis of chondroitin sulfate, as shown below in Biotest Example 1 and FIGS. 2 and 3. In addition, the glycosaminoglycan synthesized by using the C-β-D-xylopyranoside compounds of the present invention as the initiator combines with no protein components and has an extremely lower molecular weight (molecular weight: $2.0 \times 10^4$ to $3.0 \times 10^4$) as compared with normal proteoglycan (molecular weight: $2.5 \times 10^6$ or more), hence it is hard for the glycosaminoglycan to remain in tissues. Therefore, the glycosaminoglycan in a tissue culture system will be liberated into the culture medium, and in an animal body, it will be liberated from tissues into the blood stream. Thus, when the C-β-D-xylopyranoside compound of the present invention is administered to a living organism, the proteoglycan on the surface of the cell membranes constituting the tissues will decrease in quantity and the low molecular weight glycosaminoglycan (chondroitin sulfate) formed under the action of the C-β-D-xylopyranoside compounds of the present invention as an initiator will conclusively be liberated into the blood stream. Explanation of this effect can be given employing transplantable cancer cells (such as Sarcoma-180) as an example: the compound of the present invention causes the quantity of the proteoglycan on the transplantable cancer cell (Sarcoma-180) surfaces to considerably reduce, so that the cancer cell become, so to speak, a stripping state, and the immunity of the living organism to a transplantable cancer is enhanced by the immune cells. Accordingly, it is well expected that the compounds of the present invention will be useful for prevention and therapy of transplantable cancers (such as Sarcoma-180).

Further, the glycosaminoglycan (chondroitin sulfate) liberated into the blood stream has the same effects on a living organism as the chondroitin sulfate which is specially administered to the living organism from the exterior. Thus, it is expected that the compounds of the present invention will be effective for the prevention and therapy of various diseases caused by the lipid deposition onto the walls of blood vessels and the vascular sclerosis. In addition, the C-β-D-xylopyranoside series compounds of the present invention are less vulnerable to the hydrolysis by acids and enzymes, as compared with conventional O-β-D-xylopyranoside compounds. Thus, the compounds of the present invention involve no possibility of suffering from decomposition before they reach the so-called target organs. As a result, all portions administered to a living organism can function effectively. This is a valuable advantage over the conventional O-β-D-xylopyranoside compounds.

Furthermore, the compound according to this invention shows an effect of inhibition of platelet agglutination caused by several kinds of platelet agglutinating agents such as ADP, collagen, thrombin, ristocetin and epinephrine. It can therefore be expected that the compound according to this invention may be useful as a pharmaceutical for the therapy of thrombosis.

Figure 2:
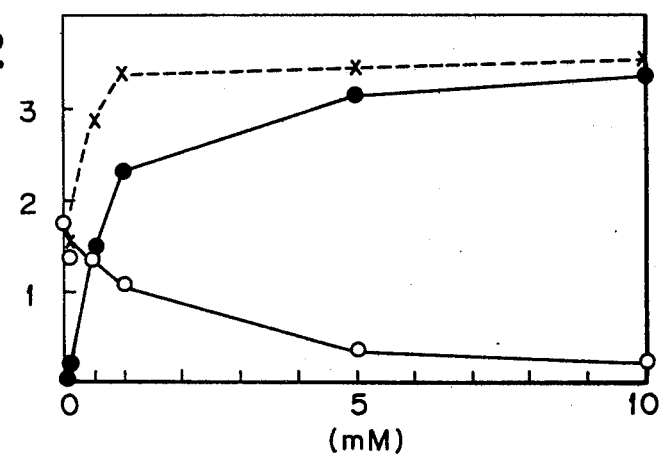
Figure 3:
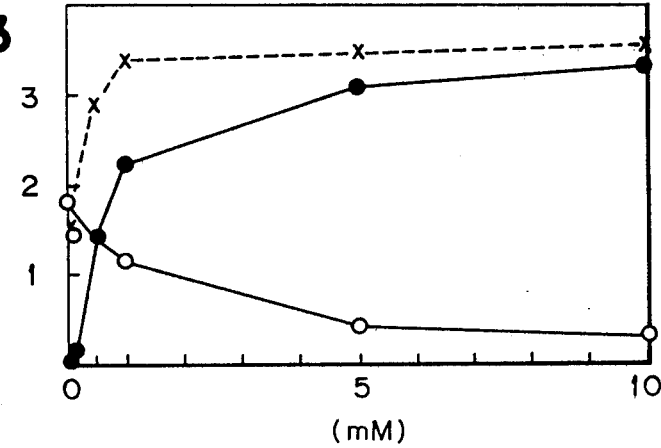

The present invention will be described in detail below with reference to the Synthesis Examples, Preparative Examples and Biotest Examples, as well as the accompanying drawings:

FIGS. 1 to 3 are graphs showing the effects of conventional O-paranitrophenyl-β-D-xylopyranoside, C-n-butyl-β-D-xylopyranoside of the present invention and C-ethyl-β-D-xylopyranoside of the present invention, respectively, on the synthesis of chondroitin sulfate.

In each Figure, the vertical axis denotes the amount of $^{35}S$ labelled chondroitin sulfate ($^{35}S$ cpm$\times 10^{-4}/\mu$mol·uronic acid), and the horizontal axis denotes the concentration (mM) of each xylopyranoside compound in the culture medium, and x----x: Total uptake amount of $^{35}S$ labelled chondroitin sulfate, ●—●: Amount of $^{35}S$ labelled chondroitin sulfate in culture medium, and o—o: Amount of $^{35}S$ labelled chondroitin sulfate in tissue.

SYNTHESIS EXAMPLE 1

Synthesis of tri-O-acetyl-C-n-butyl-β-D-xylopyranoside (tri-O-acetyl-β-D-xylopyranosyl-n-butane)

After adding 3.65 g (0.15 mole) of magnesium into a 200-ml four-necked flask, 70 ml of ether was added thereto, and the obtained mixture was stirred vigorously. Then, an ethereal solution (20 ml) containing 20.55 g (0.15 mole) of n-butyl bromide was added dropwise to the mixture over 3 hours. After the dropwise addition was completed, the resulting reaction mixture was heated under reflux for 2 hours. The reaction mixture was then cooled to room temperature, and an ethereal solution (30 ml) containing 2.95 g (0.01 mole) of tri-O-acetylxylosyl chloride (IV) was added dropwise to the reaction mixture over 30 minutes. After the dropwise addition was over, the obtained reaction mixture was heated under reflux for 5 hours. Then, the reaction mixture was cooled to room temperature and gradually poured into 200 ml of ice-water. The mixture thus obtained was then acidified with the addition of acetic acid, and the organic phase was separated. The aqueous phase was concentrated under reduced pressure and dried in a vacuum (0.01 mmHg, 100° C., 30 minutes) to give a white solid. The obtained solid was then pulverized finely and put into a 500-ml eggplant type flask. To the pulverized solid, 5 g of anhydrous sodium acetate and 100 ml of acetic anhydride were added, and the resulting reaction mixture was stirred at a temperature of 100° C. for 3 hours. After cooling the reaction mixture to room temperature, it was poured into 300 ml of ice-water and stirred overnight. The aqueous phase was then extracted once with 300 ml of ether and then twice with 100 ml of ether each time. The combined extracts were then neutralized by the addition of 100 ml of aqueous saturated sodium hydrogencarbonate and 100 g of powdered sodium hydrogencarbonate. The organic phase was separated and dried over anhydrous sodium sulfate. The dried organic phase was then concentrated under reduced pressure, and the residue was subjected to silica gel column chromatography to yield 1.3 g of tri-O-acetyl-C-n-butyl-β-D-xylopyranoside as the desired product.

Rf=0.48 [hexane—ethyl acetate (1:1)].

'HNMR(CDCl$_3$), δppm: 0.90 (t, J=6.0 Hz, CH$_3$), 1,1~1.7 (m, CH$_2$), 2.04 (s, CH$_3$CO), 3.24 (dd, J=10.0, 11.2 Hz, 1H), 3.36 (m, 1H), 4.11 (dd, J=5.2, 11.2 Hz, 1H), 4.75~5.28 (m, 3H).

SYNTHESIS EXAMPLE 2

Synthesis of tri-O-acetyl-C-n-butyl-β-D-xylopyranoside (tri-O-acetyl-β-D-xylopyranosyl-n-butane)

After adding 3.65 g (0.15 mole) of magnesium into a 200-ml four-necked flask, 70 ml of ether was added thereto, and the obtained mixture was stirred vigorously. Then, an ethereal solution (20 ml) containing 20.55 g (0.15 mole) of n-butyl bromide was added dropwise to the mixture over 3 hours. After the dropwise addition was completed, the resulting reaction mixture was heated under reflux for 2 hours. The reaction mixture was then cooled to room temperature, and an ethereal solution (30 ml) containing 4 g of tri-O-acetyl-α-D-xylosyl chloride (IV) was added dropwise to the reaction mixture over 30 minutes. After the dropwise addition was over, the obtained reaction mixture was heated under reflux for 5 hours. Then, the reaction mixture was cooled to room temperature and gradually poured into 200 ml of ice-water. The mixture thus obtained was then acidified with the addition of acetic acid, and the organic phase was separated. The aqueous phase was concentrated under reduced pressure and dried in a vacuum (0.01 mmHg, 100° C., 30 minutes) to give a white solid. The obtained solid was then pulverized finely and put into a 500-ml eggplant type flask. To the pulverized solid, 5 g of anhydrous sodium acetate and 100 ml of acetic anhydride were added, and the resulting reaction mixture was stirred at a temperature of 100° C. for 3 hours. After cooling the reaction mixture to room temperature, it was poured into 300 ml of ice-water and stirred overnight. The aqueous phase as then extracted once with 300 ml of ether and then twice with 100 ml of ether each time. The combined extracts were then neutralized by the addition of 100 ml of aqueous saturated sodium hydrogencarbonate and 100 g of powdered sodium hydrogencarbonate. The organic phase was separated and dried over anhydrous sodium sulfate. The dried organic phase was then concentrated under reduced pressure, and the residue was subjected to silica gel column chromatography to yield 1.3 g of tri-O-acetyl-C-n-butyl-β-D-xylopyranoside as the desired product.

Rf=0.48 [hexane—ethyl acetate (1:1)].

'HNMR(CDCl$_3$), δppm: 0.90 (t, J=6.0 Hz, CH$_3$), 1.1~1.7 (m, CH$_2$), 2.04 (s, CH$_3$CO), 3.24 (dd, J=10.0, 11.2 Hz, 1H), 3.36 (m, 1H), 4.11 (dd, J=5.2, 11.2 Hz, 1H), 4.75~5.28 (m, 3H).

SYNTHESIS EXAMPLE 3

Synthesis of tri-O-acetyl-C-ethyl-β-D-xylopyranoside (tri-O-acetyl-β-D-xylopyranosylethane)

Following the procedure described in Synthetic Example 1, 1.7 g of desired tri-O-acetyl-C-ethyl-β-D-xylopyranoside was obtained from 2.95 g of tri-O-acetyl-α-D-xylosyl chloride (IV) and 10.66 g (0.08 mole) of ethylmagnesium bromide.

Rf=0.53 [toluene—ethyl acetate (3:1)]

'HNMR(CDCl$_3$), δppm: 0.96 (t, J=6.8, CH$_2$CH$_3$), 1.27~1.8 (m, 2H, CH$_2$CH$_3$), 2.04 (s, 9H, CH$_3$CO), 3.22 (dd, J=10.0, 11.4 Hz, 1H, H$_{5a}$), 3.27 (m, 1H, H$_1$), 4.08 (dd, J=5.4, 11.4 Hz, 1H, H$_{5e}$), 4.67~5.35 (m, 3H, H$_2$~H$_4$).

PREPARATIVE EXAMPLE 1

Preparation of C-n-butyl-β-D-xylopyranoside (C-β-D-xylopyranosyl-n-butane)

A mixture of 399 mg (1.26 mmol) of tri-O-acetyl-C-n-butyl-β-D-xylopyranoside prepared in Synthetic Example 2 above, 10 mg of lithium hydroxide and 3 ml of anhydrous methyl alcohol was stirred at room temperature for 12 hours. After concentrating the reaction mixture under reduced pressure, the obtained residue was subjected to slica gel column chromatography to yield 240 mg (100%) of the desired product as colorless crystals.

$[\alpha]_D^{20}$ = −74.1° (c=1.16, CH$_3$OH).

Rf=0.34 [chloroform—methyl alcohol (5:1)].

'HNMR(D$_2$O), δppm: 0.90 (m, CH$_3$), 1.1~1.8 (m, CH$_2$), 3.1~3.7 (m, 5H), 3.94 (dd, J=4.2, 10.0 Hz, 1H).

mp: 100°~101° C.

PREPARATIVE EXAMPLE 2

Preparation of C-ethyl-β-D-xylopyranoside (C-β-D-xylopyranosylethane)

Following the procedure described in Preparative Example 1 above, 180 mg (97%) of desired C-ethyl-β-D-xylopyranoside was prepared from 330 mg (1.15 mmol) of tri-O-acetyl-C-ethyl-β-D-xylopyranoside obtained in Synthetic Example 3 above. The obtained product was in the form of colorless crystals and showed a melting point of 145° to 146° C.

$[\alpha]_D^{23}$ = −48° (c=1, H$_2$O).

'HNMR(D$_2$O), δppm: 0.93 (t, J=6.8, 3H, CH$_2$CH$_3$), 1.71 (m, 2H, CH$_2$CH$_3$), 3.0~4.1 (m, 6H).

BIOTEST EXAMPLE 1

Epiphysial cartilages were taken from chick embryos aged 12 days in the Tyrode's medium under ice-cooling, and excess tissues were removed therefrom. To 150 mg of cartilages corresponding to five embryos, 5 ml of BGJb [an entirely synthetic culture medium prepared according to a recipe of GIBCO (Grand Island Biological Company)] was added, followed by pre-incubation at a temperature of 37° C. After replacing the culture medium, further 1 ml of BGJb and 5μCi Na$_2^{35}$SO$_4$ were added, and the culture system was kept at 37° C. for 3 hours. The culture medium was then replaced by a fresh chase medium containing no isotope. After keeping the culture system at 37° C. for 1 hour, the culture medium was separated from the tissues. To study the effects of the xyloside compound on the synthesis of glycosaminoglycan, the xyloside compound was added in the predetermined concentration to the pre-incubation and incubation media.

After the incubation, the labeled medium containing $Na_2{}^{35}SO_4$ was combined with the chase medium. Pronase-P was added thereto in a 0.5 M tris-HCl buffer solution (pH 8.0), and the resulting mixture was digested at 50° C. for 16 hours. The digested reaction mixture was then subjected to gel filtration through a column (1.5×14 cm) packed with Bio-Gel P-2 (available from Bio-Rad Company) using a 0.2 M ammonium formate solution as elute. In this way, the Vo fraction was collected and was then freeze-dried to give crude glycosaminoglycan.

On the other hand, ice-cooled 4 M guanidine hydrochloride was added to the tissues which were previously separated from the culture medium. The resulting mixture was left to stand overnight at a temperature of −20° C., and then homogenized. The obtained homogenate was left to stand overnight at room temperature and centrifuged at a speed of 8,500 rpm to obtain a supernatant. To the obtained liquid, water was added in an amount threefold that of the supernatant. Then, a 95% ethyl alcohol (containing 1.3% of potassium acetate) was added to the resulting mixture in an amount threefold that of the mixture to obtain a precipitate. This procedure was repeated twice, and the combined precipitates were dried in a desiccator. The obtained precipitates were dissolved in a 0.02 M tris-HCl buffer solution (pH 8.0) and digested with Pronase-P (trade name) (available from Kaken Kagaku Co., Ltd.) in the manner similar to the culture medium described above, thereby obtaining crude glycosaminoglycan.

As the xyloside compound, conventional O-paranitrophenyl-β-D-xylopyranoside, and two compounds according to the present invention viz. C-n-butyl-β-D-xylopyranoside and C-ethyl-β-D-xylopyranoside were used. The effects of these xyloside compounds on the total amount of $^{35}S$ labelled glycosaminoglycan synthesized ($^{35}S$ uptake amount), the amount thereof liberated to the culture medium and the amount thereof remaining in the tissues were as shown in FIGS. 1 to 3.

Referring to FIG. 1, the $^{35}S$ uptake of glycosaminoglycan increased as the concentration of O-paranitrophenyl-β-D-xylopyranoside rose from 0.05 mM to 1.0 mM. At the concentration of 1 mM, the $^{35}S$ uptake reached 40,800 count per minute (cpm), the value which was 2.35 times that of the control. In this case, 95% of the control was liberated to the culture medium, while the amount of $^{35}S$ labelled glycosaminoglycan remaining in the tissues decreased to 11% of the control. This indicates that O-paranitrophenyl-β-D-xylopyranoside is extremely effective as the initiator for the synthesis of chondroitin sulfate as reported in J. Biochem., 74, 1069–1073 (1973).

On the other hand, with respect to the C-β-D-xylopyranosides of the present invention, the test results were as shown in FIGS. 2 and 3. As shown in these Figures, the total $^{35}S$ uptake amount of glycosaminoglycan increased as the concentration of the xyloside compounds rose, like the conventional compound described above. At the same time, the amount of $^{35}S$ labelled glycosaminoglycan liberated into the culture medium increased, while the amount thereof remaining in the tissues decreased. This indicates that, although a higher concentration of the C-β-D-xylopyranosides of the present invention is required compared with the conventional O-β-D-xylopyranoside compound, the compounds according to the present invention are excellent initiators for the synthesis of chondroitin sulfate.

BIOTEST EXAMPLE 2

Toxicity of the compound according to this invention

The acute toxicity of the compound according to this invention was determined by forced oral or intraperitoneal administration thereof to ddY mice.

To prepare each specimen to be administered, a predetermined amount of each compound shown in Table 1 was dissolved in a physiological saline or suspended in a 0.2% solution of carboxymethylcellulose in a physiological saline. Each specimen was administered orally to a ddY mouse via its stomach tube or injected intraperitoneally.

The presence or absence of the symptoms of death was observed for 7 days after administration, and $LD_{50}$ of each compound was determined from the mortality accumulated to the 7th day of the administration, according to the graphic method of Litchfield-Wilcoxon.

The results are shown in Table 1.

TABLE 1

| Compound | $LD_{50}$ through oral (po) or intraperitoneal (ip) administration | |
|---|---|---|
| | $LD_{50}$ (po) (mg/kg body weight) | $LD_{50}$ (ip) (mg/kg body weight |
| C—Ethyl-β-D-xylopyranoside | 6900 | 2400 |
| C—n-Butyl-β-D-xylopyranoside | 5800 | 2400 |

BIOTEST EXAMPLE 3

Activity against a transplantable cancer, Sarcoma-180

Sarcoma-180 cells ($1 \times 10^6$ cells) were inoculated subcutaneously into the back skin of each of ICR-JCL mice.

Chemotherapy was given intraperitoneally 24 hrs. after inoculation and performed once a day for 10 days. Each specimen to be administered was prepared by dissolving or suspending 30 mg of each compound according to this invention in 1 ml of a pysiological saline or in 1 ml of a 0.2% solution of carboxymethylcellulose in a physiological saline, respectively.

All the solutions and the suspensions thus prepared were injected at a volume of 0.1 ml as a single dose (100 mg/Kg).

The activity against Sarcoma-180 was evaluated in terms of the inhibition ratio (I.R.) (%) and shown in Table 2.

The inhibition ratio (%) was calculated according to the following equation:

$$I.R. = (1 - T/C) \times 100\%$$

wherein T represents the mean weight of the tumor Sarcoma-180 in a tested group of mice; and C represents the mean weight of the tumor in a control group of mice.

TABLE 2

| Compound | Activity against Sarcoma-180 I.R. (%) |
|---|---|
| C—Ethyl-β-D-xylopyranoside | 52.8 |
| C—n-Butyl-β-D-xylopyranoside | 69.2 |

As is clear from Table 2, it can be understood that all the compounds of this invention exhibit the activity against Sarcoma-180.

From the data of LD$_{50}$ and I.R. as shown above, it can be understood that the transplantable cancer by Sarcoma-180 in mice is inhibited or alleviated by 50% by administering one of the compounds according to this invention in a dose of about 100 mg/kg body weight per day through interperitoneal administration.

BIOTEST EXAMPLE 4

Inhibitory effect against platelet agglutinating agents

Inhibitory activities of each compound of this invention against platelet agglutinating agents (ADP, collagen, thrombin, ristocetin and epinephrine) were investigated according to the method using a microscope.

(1) Preparation of PRP (Platelet Rich Plasma)

PRP was prepared by mixing a 3.8% aqueous sodium citrate and a human vein blood at a ratio of 1:9; centrifuging the mixture at 700 r.p.m. for 10 minutes; and then collecting the supernatant.

(2) Preparation of PPP (Platelet Poor Plasma)

The residue remaining after collection of the PRP mentioned above was subjected further to centrifugation at 3000 r.p.m. for 10 minutes and then collected the supernatant to obtain PPP.

(3) Platelet agglutinating agents

Following solutions were employed for the test.
a. ADP, (2 μM/ml solution)
b. collagen, (0.25 μM/ml solution)
c. thrombin, (0.25 U/ml solution)
d. ristocetin, (1.5 mg/ml solution)
e. epinephrine, (2 μg/ml solution)

(4) Test procedure

In each well of a Multidish (Nunc Multidish having 24 wells) was placed 0.2 ml of PRP (containing $3.0 \times 10^5$ platelet cells/cmm).

Thereto was added 50 μl of a specimen solution containing 10 mM of the compound according to this invention, and the mixture was stirred at 37° C. for 2 minutes. To the mixture was added 10 μl of each solution of the platelet agglutinating agent mentioned above, and the result was observed by using a microscope 1 minute and then 5 minutes thereafter.

The degree of agglutination was expressed by using marks +, ++, +++, etc., according to the method by Fukutake et al [Katsuhiro Fukutake, Iwao Yamaguchi: Blood and Blood Vessel, Volume 6, No. 7, pp. 55~60 (1975)].

The results are shown in Table 3.

TABLE 3

| Specimen (conc.) | | Agglutinant | State of agglutination | |
|---|---|---|---|---|
| | | | 1 min. | 5 min. |
| Control | (0) | ADP | ++ | +++ |
| | (0) | collagen | ++ | +++ |
| | (0) | thrombin | ++ | +++ |
| | (0) | ristocetin | ++ | +++ |
| | (0) | epinephrine | ++ | +++ |
| C—Ethyl-β-D-xylopyranoside | (10 mM) | ADP | ± | ± |
| | (") | collagen | ± | ± |
| | (") | thrombin | ± | ± |
| | (") | ristocetin | ± | ± |
| | (") | epinephrine | ± | ± |
| C—n-Butyl-β-D-xylopyranoside | (10 mM) | ADP | ± | ± |
| | (") | collagen | ± | ± |
| | (") | thrombin | ± | ± |
| | (") | ristocetin | ± | ± |
| | (") | epinephrine | ± | ± |

We claim:
1. C-β-D-xylopyranoside series compounds having the general formula:

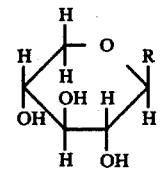

in which R denotes a lower alkyl group having from 1 to 5 carbon atoms.
2. The compound of claim 1, wherein R is methyl.
3. The compound of claim 1, wherein R is ethyl.
4. The compound of claim 1, wherein R is n-propyl.
5. The compound of claim 1, wherein R is isopropyl.
6. The compound of claim 1, wherein R is n-butyl.
7. The compound of claim 1, wherein R is isobutyl.
8. The compound of claim 1, wherein R is sec-butyl.
9. The compound of claim 1, wherein R is tert-butyl.
10. The compound of claim 1, wherein R is n-pentyl.
11. The compound of claim 1, wherein R is isopentyl.

* * * * *